(12) United States Patent
Jeong et al.

(10) Patent No.: US 9,505,757 B2
(45) Date of Patent: Nov. 29, 2016

(54) PHARMACEUTICAL COMPOSITION COMPRISING BICYCLIC PYRIDINOL DERIVATIVES FOR PREVENTING OR TREATING DISEASES CAUSED BY ANGIOGENESIS

(71) Applicant: Research Cooperation Foundation of Yeungnam University, Gyeongsan-si, Gyeongsangbuk-do (KR)

(72) Inventors: Byeong Seon Jeong, Daegu (KR); Jung Ae Kim, Daegu (KR); You Ra Kang, Gyeongsangbuk-do (KR); Tae Gyu Nam, Gyeonggi-do (KR); Jin Mo Ku, Gyeonggi-do (KR); Ned A. Porter, Nashville, TN (US)

(73) Assignee: RESEARCH COOPERATION FOUNDATION OF YEUNGNAM UNIVERSITY, Gyeongsan-Si, Gyeongsangbuk-Do (KR)

( * ) Notice: Subject to any disclaimer, the term of this patent is extended or adjusted under 35 U.S.C. 154(b) by 0 days.

(21) Appl. No.: 14/801,842

(22) Filed: Jul. 17, 2015

(65) Prior Publication Data
US 2015/0320729 A1 Nov. 12, 2015

Related U.S. Application Data

(63) Continuation of application No. 14/362,917, filed as application No. PCT/KR2012/010630 on Dec. 7, 2012, now abandoned.

(30) Foreign Application Priority Data

Dec. 8, 2011 (KR) .................. 10-2011-0131290
Dec. 7, 2012 (KR) .................. 10-2012-0141581

(51) Int. Cl.
| | | |
|---|---|---|
| *A61K 31/437* | (2006.01) | |
| *C07D 471/04* | (2006.01) | |
| *A61K 9/20* | (2006.01) | |
| *A61K 31/4375* | (2006.01) | |
| *A61K 31/44* | (2006.01) | |

(52) U.S. Cl.
CPC ........... *C07D 471/04* (2013.01); *A61K 9/2018* (2013.01); *A61K 9/2059* (2013.01); *A61K 31/437* (2013.01); *A61K 31/4375* (2013.01); *A61K 31/44* (2013.01)

(58) Field of Classification Search
None
See application file for complete search history.

(56) References Cited

PUBLICATIONS

Howington "Treatment of Stage I and II Non-small Cell Lung Cancer Diagnosis and Management of Lung Cancer, 3rd ed: American College of Chest Physicians Evidence-Based Clinical Practice Guidelines" Chest 2013; 143(5)(Suppl):e278S-e313S.*
Socinski "Treatment of Stage IV Non-small Cell Lung Cancer Diagnosis and Management of Lung Cancer, 3rd ed: American College of Chest Physicians Evidence-Based Clinical Practice Guideline" Chest 2013; 143(5)(Suppl):e341S-e368S.*
Jett Treatment of Small Cell Lung Cancer Diagnosis and Management of Lung Cancer, 3rd ed: American College of Chest Physicians Evidence-Based Clinical Practice Guidelines Chest 2013; 143(5)(Suppl):e400S-e419S.*
Damia "Contemporary pre-clinical development of anticancer agents—What are the optimal preclinical models?" European Journal of Cancer 2009, 45, 2768-2781.*
Ocana, A. "Preclinical development of molecular targeted agents for cancer" Nat. Rev. Clin. Oncol. 2011, 8, 200-209.*
Sharma "Cell line-based platforms to evaluate the therapeutic efficacy of candidate anticancer agents" Nature Reviews Cancer Apr. 2010, vol. 10, 241-253.*
Begley "Antioxidants including vitamin E can promote lung cancer: study" Reuters Online Wed Jan. 29, 2014 "http://www.reuters.com/article/us-antioxidants-idUSBREA0S1QV20140129" accessed Feb. 3, 2016.*
Cimpean "The chick embryo chorioallantoic membrane as a model to study tumor metastasis" Angiogenesis (2008) 11:311-319.*
Byeong Seon Jeong et al., New scope in angiogenesis: Role of vascular endothelial growth factor(VEGF), NO, lipid peroxidation, and vitamin E in the pathophysiology of pre-eclampsia among Egyptian females, Clinical Biochemistry 34 (2001) 323-329.
Tae-Gyu Nam et al., New synthetic route to N-tocopherol derivatives: synthesis of pyrrolopyridinol analogue of a tocopherol from pyridoxine, Organic & Biomolecular Chemistry, 2011, 9, 1749.
Remigiusz Serwa et al., Preparation and Investigation of Vitamin B6-Derived Aminopyridinol Antioxidants, Chem. Eur. J. 2010, 16, 14106-14114.
Masuko Ushio-Fukai, Redox signaling in angiogenesis: Role of NADPH oxidase, Cardiovascular Research 71 (2006) 226-235.
Tae-Gyu Nam et al., Tetrahydro-1,8-naphthyridinol Analogues of r-Tocopherol as Antioxidants in Lipid Membranes and Low-Density Lipoproteins, J. Am. Chem. Soc. 2007, 129, 10211-10219.
International Search Report for PCT/KR2012/010630 mailed Mar. 29, 2013 from Korean Intellectual Property Office.
Auerbach "Angiogenesis Assays: A Critical Overview" Clinical Chemistry 2003, 49, 32-40.
Anghel et. al. "Antioxidants: not heaven-sent" Harvard Science Review Spring 2010 32-34.
Organic & Biomolecular Chemistry vol. 9 | No. 6 | Mar. 21, 2011 , Front Cover.

(Continued)

*Primary Examiner* — David K O'Dell
(74) *Attorney, Agent, or Firm* — Revolution IP, PLLC

(57) ABSTRACT

Disclosed is a pharmaceutical composition including a bicyclic pyridinol derivative as an active ingredient for preventing or treating diseases caused by angiogenesis. The bicyclic pyridinol derivative expressed by Chemical Formula 1 can be effectively used as a drug for preventing and treating diseases caused by angiogenesis since it inhibits neovascularization in a chorioallantoic membrane model.

2 Claims, 7 Drawing Sheets

(56) References Cited

PUBLICATIONS

Grazia 0 'Onofrio "Advances in the identification of g-secretase inhibitors for the treatment of Alzheimer's disease" Expert Opinion on Investigational Drugs 2012, 7, 20-37.

Yuzwa "O-GlcNAc and neurodegeneration: biochemical mechanisms and potential roles in Alzheimer's disease and beyond" Chem. Soc. Rev., 2014, 43, 6839.

Kristal "Baseline Selenium Status and Effects of Selenium and Vitamin E Supplementation on Prostate Cancer Risk" J Natl Cancer Inst 2014 106(3): djt456 1-8.

Johnson, et. al. "Relationships between drug activity in NCI preclinical in vitro and in vivo models and early clinical trials." British Journal of Cancer 2001, 84, 1424-1431.

Simone, Oncology: Introduction, Cecil Textbook of Medicine, 20th Edition, 1996 vol. 1, pp. 1004-1010.

Kuenen "Efficacy and Toxicity of the Angiogenesis Inhibitor SU5416 as a Single Agent in Patients with Advanced Renal Cell Carcinoma, Melanoma, and Soft Tissue Sarcoma" Clinical Cancer Research vol. 9, 1648-1655, May 2003.

Jhee et. a l. "Beta-amyloid therapies in Alzheimer's disease" Expert Opinion on Investigational Drugs 2001, 10, 593-605.

Randolph M. Howes "The Free Radical Fantasy a Panoply of Paradoxes" Annals of the New York Academy of Sciences (2006) 1067: 22-26.

Hook V. Y. H. " Neuroproteases in Peptide Neurotransmission and Neurodegenerative Diseases Applications to Drug Discovery Research" Biodrugs 2006, 20, 105-119.

\* cited by examiner

Fig. 8

| Treatment | | Angiogenesis Inhibition (%) | Tumor growth inhibition (%) |
|---|---|---|---|
| PBS | | | |
| α-tocopherol (μM) | 0.1 | 0.6 ± 2.0 | 8.4 ± 3.9 |
| | 1 | 0.3 ± 2.3 | 10.4 ± 3.8 |
| | 10 | 14.5 ± 2.8 | 23.9 ± 16.1 |
| | 100 | 29.6 ± 0.8* | 35.5 ± 8.2* |

| | | | |
|---|---|---|---|
| PBS | | | |
| Comp. 12 (μM) | 0.0001 | 17.3 ± 10.3 | 16.1 ± 11.6 |
| | 0.001 | 22.9 ± 5.0* | 44.7 ± 13.0* |
| | 0.01 | 33.9 ± 1.6* | 49.4 ± 6.6* |
| | 0.1 | 50.0 ± 2.1* | 53.3 ± 9.9* |

PHARMACEUTICAL COMPOSITION COMPRISING BICYCLIC PYRIDINOL DERIVATIVES FOR PREVENTING OR TREATING DISEASES CAUSED BY ANGIOGENESIS

CROSS REFERENCE TO PRIOR APPLICATIONS

This application is a continuation application of U.S. patent application Ser. No. 14/362,917 filed Sep. 5, 2014, which is a 371 National Stage Application of International Patent Application No. PCT/K2012/010630 filed Dec. 7, 2012, which claims priority to Korean Patent Application Nos. 10-2011-0131290 filed Dec. 8, 2011 and 10-2012-0141581 filed Dec. 7, 2012, which are hereby incorporated by reference in their entirety.

BACKGROUND

The present invention relates to a pharmaceutical composition comprising a bicyclic pyridinol derivative for preventing or treating diseases caused by angiogenesis.

Angiogenesis is a process of forming new capillary blood vessels from pre-existing microvessels. Angiogenesis normally occurs during embryonic development, tissue regeneration, wound healing, and corpus luteum development that is a cyclical change in female reproductive system; in any case, angiogenesis is strictly regulated to progress (Folkman J et al., *Int. Rev. Exp. Pathol.*, 16, pp207-248, 1976).

The vascular endothelial cells are growing slowly and do not divide well relatively as compared with other types of cells in adult body. Angiogenesis is a process that generally includes degradation of a vascular basement membrane by proteases released by stimuli of proangiogenic factors; migration and proliferation of vascular endothelial cells; tubular formation due to differentiation of vascular endothelial cells; reconstruction of blood vessels; and generation of new capillary blood vessels.

However, there are diseases induced by angiogenesis that is not regulated autonomously but grows morbidly. Such diseases associated with angiogenesis occurring in pathological conditions include hemangioma, angiofibroma, vascular malformation and cardiovascular diseases, such as arteriosclerosis, vascular adhesion, and scleroedema. Ocular diseases associated with angiogenesis include corneal graft angiogenesis, neovascular glaucoma, diabetic retinopathy, corneal diseases induced by new blood vessels, macular degeneration, pterygium, retinal degeneration, retrolental fibroplasia, granular conjunctivitis, and the like. Furthermore, angiogenesis-related diseases may include chronic inflammatory diseases such as arthritis, cutaneous diseases such as psoriasis, capillarectasia, pyogenic granuloma, seborrheic dermatitis, acne, Alzheimer's disease, and obesity. Tumor growth and metastases are necessarily dependent on angiogenesis (D'Amato R J et al., *Ophthalmology*, 102(9), pp1261-1262, 1995; Arbiser J L, *J. Am. Acad. Dermatol.*, 34(3), pp486-497, 1996; O'Brien K D et al. *Circulation*, 93(4), pp672-682, 1996; Hanahan D et al., Cell, 86, pp353-364, 1996).

Especially, angiogenesis plays an important role in growth and metastasis of cancer cells. Tumor is supplied with nutrition and oxygen necessary for growth and proliferation through new blood vessels, and the new blood vessels infiltrating into the tumor allow the cancer cells being metastasized to enter the blood circulation system and thus support metastasis of the cancer cells (Folkman and Tyler, *Cancer Invasion and metastasis*, Biologic mechanisms and Therapy (S. B. Day ed.) Raven press, New York, pp94-103, 1977; Polverini P J, *Crit. Rev. Oral. Biol. Med.*, 6(3), pp230-247, 1995). The major cause of death in cancer patients is metastasis, and the reasons why the chemotherapies or immunotherapies being used clinically at present do not contribute to an increase in a survival rate of cancer patients is directed to metastasis of cancer.

Arthritis, a typical disease in inflammatory diseases, is initiated as an autoimmune disorder. Along with progression of the disease, chronic inflammation occurring in the synovial cavity between joints induces angiogenesis to destroy the cartilage. That is, proliferations of synovial cells and vascular endothelial cells in the synovial cavity are activated by cytokines that induce inflammations, resulting in development of angiogenesis. Finally, the articular cartilage playing a role of a cushion is destroyed by articular pannus as a connective tissue layer formed in a cartilaginous part (Koch A E et al., *Arthritis. Rheum.*, 29, pp471-479, 1986; Stupack D G et al., *Braz J. Med. Biol. Res.*, 32(5), pp578-581, 1999; Koch A E, *Atrhritis. Rheum.*, 41(6), pp951-962, 1998).

Many ocular diseases, from which millions of people are losing their eyesight all over the world every year, result mainly from angiogenesis (Jeffrey M I et al., *J. Clin. Invest.*, 103, pp1231-1236, 1999). Typical diseases resulting from angiogenesis include macular degeneration, diabetic retinopathy, and the like that occur commonly in old age, premature infant's retinopathy, neovascular glaucoma, corneal diseases induced by new blood vessels, and the like (Adamis A P et al., *Angiogenesis*, 3, pp9-14, 1999). Among them, diabetic retinopathy that is one of the diabetic complications and a disease that retinal capillaries invade vitreous body to become blind.

Psoriasis characterized by red spots and scaly skin is a chronic proliferative disease occurring in skin and is accompanied with pain and malformation. Normally, keratinocytes proliferate once a month, however, in a psoriasis patient, the keratinocytes proliferate at least once a week. For such rapid proliferation, a large quantity of blood is required, resulting in active angiogenesis (Folkman J, *J. Invest. Dermatol.*, 59, pp40-48, 1972).

Since it is possible to apply angiogenesis inhibitors to agents for treating various diseases associated with angiogenesis, in recent years, a variety of studies aimed at treating such diseases by inhibiting angiogenesis have been actively conducted. Since such angiogenesis inhibitors should be administrated to patients for a long time, the most ideal inhibitor is one that should have low toxicity and can be orally administrated. Accordingly, there has been a demand for development of drugs that have low toxicity as angiogenesis inhibitors.

SUMMARY

Hence, the inventors of the present invention confirmed that a bicyclic pyridinol derivative having a specific structure is highly effective in inhibiting angiogenesis, and, thus, completed the present invention.

Therefore, an object of the present invention is to provide a pharmaceutical composition containing a bicyclic pyridinol derivative as an active ingredient for preventing or treating diseases caused by angiogenesis.

The present invention provides a pharmaceutical composition containing a bicyclic pyridinol derivative expressed by the following Chemical Formula 1 for preventing or treating diseases caused by angiogenesis:

[Chemical Formula 1]

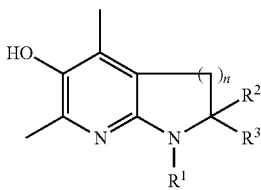

In the above formula, $R^1$ to $R^3$ may be identical with or different from one another and may be any one of hydrogen, C1 to C16 alkyl, acyloxymethyl, or trimethyltridecyl, and n may be an integer of 1 to 2.

In the bicyclic pyridinol derivative, $R^1$ may be any one of hydrogen, methyl, ethyl, or n-$C_{16}H_{33}$, $R^2$ may be any one of hydrogen or methyl, $R^3$ is one of hydrogen, methyl, n-butyl, t-butyl, acyloxymethyl, or trimethyltridecyl

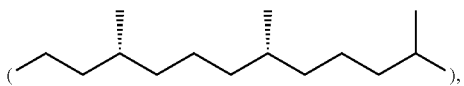

and n may be an integer of 1 to 2.

Further, the bicyclic pyridinol derivative may be preferably a compound expressed by the following Chemical Formula 2 and more preferably a compound expressed by the following Chemical Formula 3:

[Chemical Formula 2]

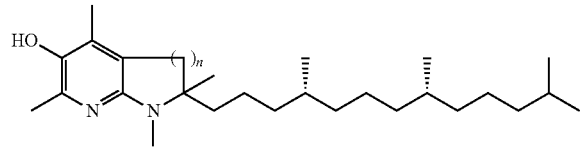

In the above formula, n may be an integer of 1 to 2,

[Chemical Formula 3]

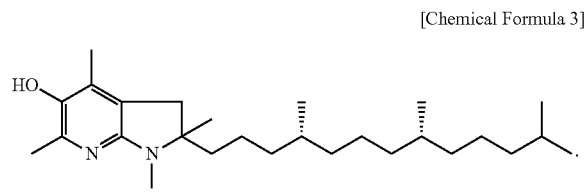

A bicyclic pyridinol derivative according to the present invention can be effectively used as a drug for preventing and treating diseases caused by angiogenesis since it inhibits neovascularization induced by an angiogenesis inducer such as a vascular endothelial growth factor in a chicken chorioallantoic membrane model.

BRIEF DESCRIPTION OF THE DRAWINGS

FIG. 8 illustrates an observation result of angiogenesis caused by tumorigenesis by inoculating A549 lung cancer cells to a CAM and a tumor growth inhibitory effect.

DETAILED DESCRIPTION

Figure 1:
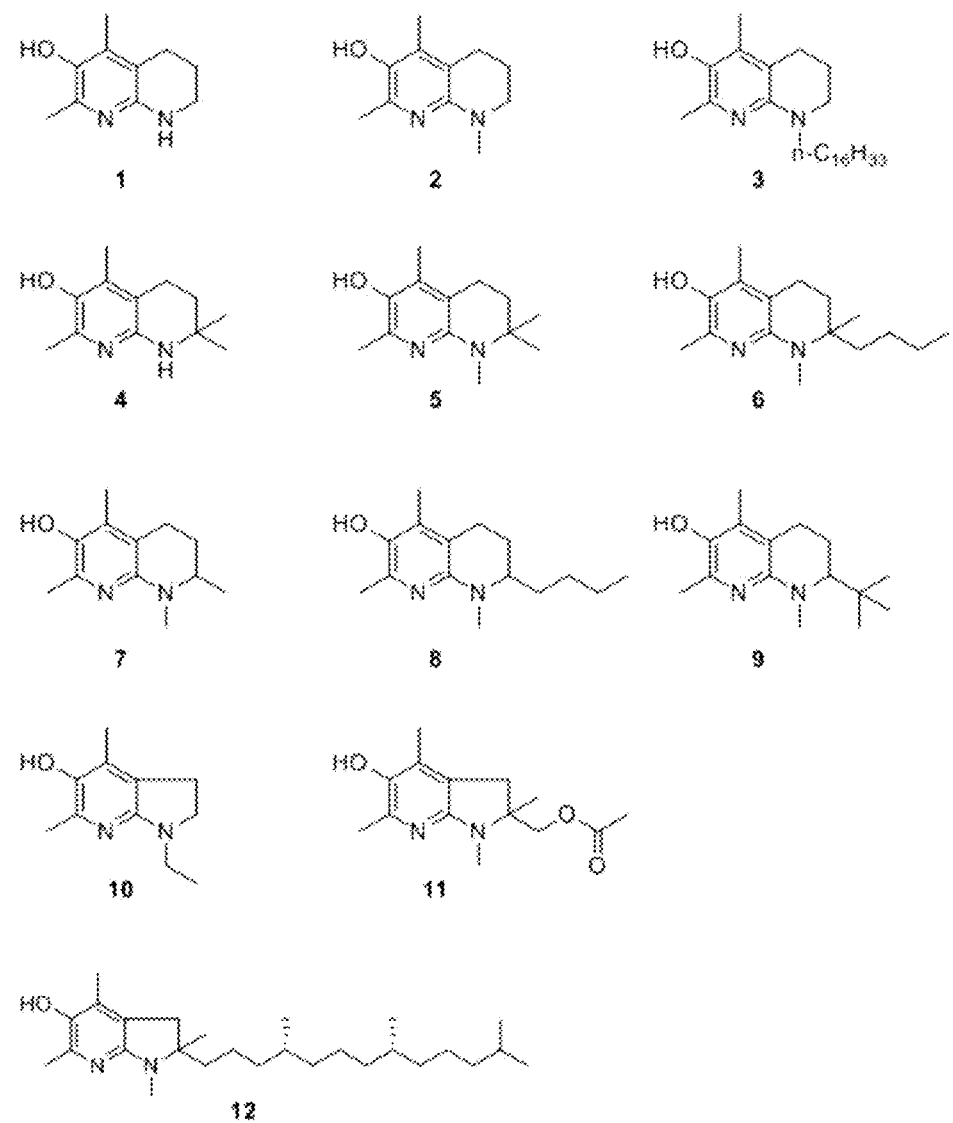
FIG. 1 illustrates chemical formulas of bicyclic pyridinol derivatives according to an example of the present invention.

In order to achieve the above object, the present invention provides a pharmaceutical composition containing a bicyclic pyridinol derivative expressed by the following Chemical Formula 1 for preventing or treating diseases caused by angiogenesis:

[Chemical Formula 1]

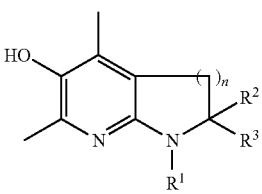

In the above formula, $R^1$ to $R^3$ may be identical with or different from one another and may be any one of hydrogen, C1 to C16 alkyl, acyloxymethyl, or trimethyltridecyl, and n may be an integer of 1 to 2.

In the bicyclic pyridinol derivative, $R^1$ may be any one of hydrogen, methyl, ethyl, or n-$C_{16}H_{33}$, $R^2$ may be any one of hydrogen or methyl, $R^3$ is one of hydrogen, methyl, n-butyl, t-butyl, acyloxymethyl, or trimethyltridecyl

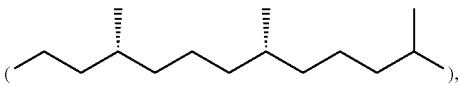

and n may be an integer of 1 to 2.

Further, the bicyclic pyridinol derivative may be preferably a compound expressed by the following Chemical Formula 2 and more preferably a compound expressed by the following Chemical Formula 3:

[Chemical Formula 2]

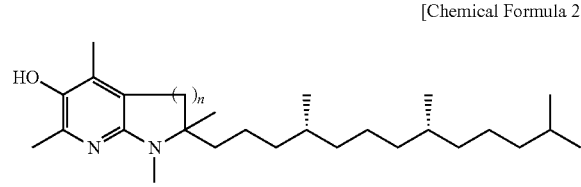

In the above formula, n may be an integer of 1 to 2.

[Chemical Formula 3]

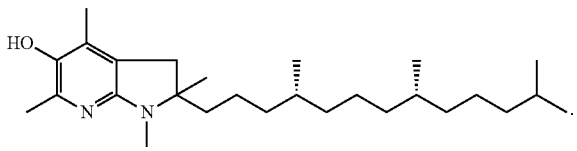 [SMILES: Cc1nc2c(c(C)c1O)CC(C)(CCC[C@H](C)CCC[C@H](C)CCCC(C)C)N2C]

The diseases caused by angiogenesis may be selected from the group consisting of rheumatic arthritis, osteoarthritis, septic arthritis, psoriasis, corneal ulcer, senile macular degeneration, diabetic retinopathy, proliferative vitreous body retinopathy, premature retinopathy, ocular inflammation, conical cornea, Sjogren's syndrome, myopia eye tumor, cornea graft rejection, abnormal wound healing, bone disease, proteinuria, abdominal aortic aneurysm disease, regressive cartilage loss due to traumatic joint injury, demyelinating disease of nervous system, hepatic cirrhosis, glomerular disease, premature rupture of embryonic membrane, inflammatory bowel disease, periodontal membrane disease, arteriosclerosis, restenosis, inflammatory disease of central nervous system, Alzheimer's disease, skin aging, and infiltration metastasis of cancer.

A bicyclic pyridinol derivative of the present invention can be effectively used as a drug for preventing and treating diseases caused by angiogenesis since it inhibits angiogenesis induced by an angiogenesis inducer such as a vascular endothelial growth factor in a chicken chorioallantoic membrane model.

Doses and ways of application of a pharmaceutical composition containing a bicyclic pyridinol derivative of the present invention may vary depending on the formulations and the use purposes thereof.

The pharmaceutical composition containing a bicyclic pyridinol derivative of the present invention may contain a bicyclic pyridinol derivative in the amount of 0.1 to 50 weight % with respect to the total weight of the composition.

Further, the pharmaceutical composition containing a bicyclic pyridinol derivative of the present invention may further contain suitable carriers, excipients, or diluents commonly used in preparing pharmaceutical compositions.

Examples of the carriers, excipients, or diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil.

The pharmaceutical composition containing a bicyclic pyridinol derivative of the present invention may be prepared in oral formulations including powders, granules, tablets, capsules, suspensions, emulsions, syrups, aerosols, and the like, agents for external application, suppository and sterilizing injection solutions by respective methods commonly used.

In the case of being formulated, the pharmaceutical composition is prepared using diluents or excipients such as fillers, extenders, bonding agents, humectants, disintegrants, surfactants, etc. Solid dosage forms for oral administration include tablets, pills, powders, granules, capsules, and the like. Such solid dosages are prepared by mixing the compound with at least one excipient, such as starch, calcium carbonate, sucrose or lactose, and gelatin.

In addition to simple excipients, lubricants such as magnesium stearate, and talc may be used. Liquid dosage forms for oral administration, such as suspensions, internal solutions, emulsions, and syrups, may contain commonly used simple diluents, for example, water and liquid paraffin, as well as various excipients, for example, humectants, sweeteners, aromatics, preservatives, and the like. Dosage forms for parenteral administration include sterilized aqueous solutions, non-aqueous solvents, suspensions, emulsions, lyophilized agents, suppositories, and the like. Non-aqueous solvents and suspensions may be prepared using propylene glycol, polyethylene glycol, vegetable oils such as olive oil, or injectable esters such as ethyl oleate. As bases for suppositories, witepsol, macrogol, Tween 61, cacao oil, laurinum, and glycerogelatine can be used.

The dosages of the bicyclic pyridinol derivative of the present invention may vary depending on age, sex, and weight of a patient. 0.001 to 100 mg/kg or preferably, 0.01 to 10 mg/kg of the bicyclic pyridinol derivative can be administrated once or several times a day. Moreover, the dosages of the compound may be increased and decreased depending on an administration path, severity of disease, sex, weight, age, and the like. Accordingly, the dosages do not limit the scope of the present invention in any aspect.

The pharmaceutical composition can be administrated to mammals such as rats, mice, livestock, and humans through various paths. For example, it can be administered by any kinds of predictable administration methods such as oral, rectal or intravenous, intramuscular, cutaneous, intrauterine or intracerebroventricular injection administrations.

The bicyclic pyridinol derivative according to the present invention has 50% lethality ($LC_{50}$) of 2 g/kg or more with secured stability and thus can be used in the pharmaceutical composition of the present invention.

Hereinafter, the present invention will be explained in more detail with reference to the following Examples. However, the present invention is not limited to these Examples.

Example 1

Synthesis of Bicyclic Pyridinol Derivative

The following Table 1 lists and FIG. 1 illustrates bicyclic pyridinol derivatives according to an example, and each of the bicyclic pyridinol derivatives were prepared by synthesizing the compounds by the methods described in references, respectively.

[Chemical Formula 1]

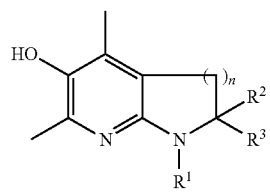

TABLE 1

| Compound | N | $R^1$ | $R^2$ | $R^3$ | Reference |
|---|---|---|---|---|---|
| 1 | 2 | H | H | H | Chem. Eur. J., 2010, 16, 14106-14114 |
| 2 | 2 | Me | H | H | Chem. Eur. J., 2010, 16, 14106-14114 |

TABLE 1-continued

| Compound | N | R$^1$ | R$^2$ | R$^3$ | Reference |
|---|---|---|---|---|---|
| 3 | 2 | n-C$_{16}$H$_{33}$ | H | H | Chem. Eur. J., 2010, 16, 14106-14114 |
| 4 | 2 | H | Me | Me | Synthesis, 2005, 1397-1404 |
| 5 | 2 | Me | Me | Me | Synthesis, 2005, 1397-1404, J. Am. Chem. Soc., 2007, 129, 10211-10219 |
| 6 | 2 | Me | Me | n-Bu | J. Am. Chem. Soc., 2007, 129, 10211-10219 |
| 7 | 2 | Me | H | Me | J. Am. Chem. Soc., 2007, 129, 10211-10219 |
| 8 | 2 | Me | H | n-Bu | J. Am. Chem. Soc., 2007, 129, 10211-10219 |
| 9 | 2 | Me | H | t-Bu | J. Am. Chem. Soc., 2007, 129, 10211-10219 |
| 10 | 1 | Et | H | H | Org. Biomol. Chem., 2011, in press. DOI: 10.1039/c1ob05144j |
| 11 | 1 | Et | Me | CH$_2$OCOMe | Org. Biomol. Chem., 2011, in press. DOI: 10.1039/c1ob05144j |
| 12 | 1 | Me | Me | C16* | Org. Biomol. Chem., 2011, 9, 1749-1755 |

Me represents methyl,
Et represents ethyl,
Bu represents butyl, and
C16* represents

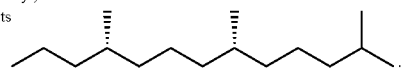

Experimental Example 1

Angiogenesis Inhibitory Effects Via CAM Assay

To examine angiogenesis inhibitory effects in vivo, a chorioallantoic membrane (CAM) assay was carried out (Nguyen M et al., *Microvascular Res.*, 47, pp31-40, 1994).

Fertilized chicken eggs were cultured keeping the temperature at 37° C. and the relative humidity at 55%. On the tenth day, the first small hole was made in the region of air sac and the second hole was dug in the flat region of egg, where a window was to be made, using a hypodermic needle (Greencross Medical Science, Korea).

Each egg was deflated through the first hole in the region of the air sac so that the chorioallantoic membrane (CAM) was split from the egg shell. Subsequently, a window was made by cutting this region using a grinding wheel (Multi-pro 395JA, Dremel, Mexico).

Then, a whatman filter disc #1 (Whatman Inc. USA) was treated with 3 mg/ml of cortisone acetate and dried. The filter disc was drenched with a vascular endothelial growth factor (VEGF) in a concentration of 20 ng/CAM.

The filter disc was put on the vessels through the previously made window, and a compound 12 of Example was dissolved in dimethylsulfoxide (DMSO) and diluted with phosphate buffered saline (PBS) to treat by concentrations.

After 3 days from the drug treatment, the CAMs, on which the filter disc was placed, were separated and washed with PBS to take images using a stereomicroscope (Stemi SV6 stereomicroscope, Carl Zeiss, Germany) and Image-Pro Plus software (Media Cybernetics; Silver Spring, Md., USA). Then, the number of branches was counted and the result data were analyzed.

As a result thereof, as listed in the following Table 2, it could be confirmed that an increase in neovascularization induced by the VEGF was decreased in a concentration-dependent manner due to the treatment with the compound 12 according to the present invention. In particular, according to comparison in angiogenesis inhibitory effect between the compound 12 and SU4312, batimastat, and α-tocopherol, the compound 12 had an excellent angiogenesis inhibitory effect capable of inhibiting angiogenesis in a lower concentration than the other compounds.

TABLE 2

| Experimental group | | Number of branches/ Main vessel | Inhibition rate (%) |
|---|---|---|---|
| PBS | | 14.4 ± 2.7 | — |
| VEGF (20 ng/CAM) | | 52.2 ± 2.7 | — |
| VEGF (20 ng/CAM)+ | SU4312 (1 μg/CAM, 378 μM) | 24 ± 4.6$^\#$ | 74.6 ± 12.1 |
| | Batimastat (1 μg/CAM, 209 μM) | 19.9 ± 2.87$^\#$ | 78.4 ± 7.4 |
| | α-tocopherol (3 ng/CAM, 0.7 μM) | 32.3 ± 3.5 | 45.1 ± 9.3 |
| | α-tocopherol (100 ng/CAM, 23 μM) | 24.3 ± 2.7$^\#$ | 64.4 ± 14.2 |
| | Compound 12 (0.004 ng/CAM, 1 nM) | 28 ± 4.7$^\#$ | 64.0 ± 12.5 |
| | Compound 12 (0.04 ng/CAM, 10 nM) | 25.2 ± 2.4$^\#$ | 71.4 ± 6.4 |

Figure 2:
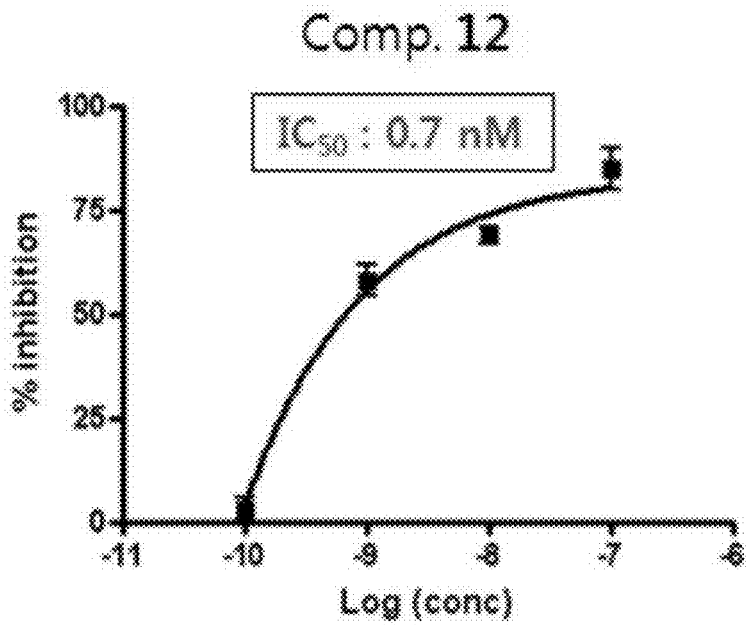
FIG. 2 is a value of $IC_{50}$ obtained by treating a compound 12 with a CAM by concentrations.

Further, IC$_{50}$ was obtained by treating the compound 12 with a CAM by concentrations, and the IC$_{50}$ was 0.7 nM (FIG. 2).

Experimental Example 2

VEGF-Induced Growth Inhibitory Effect in HUVEC Cells

Figure 3:
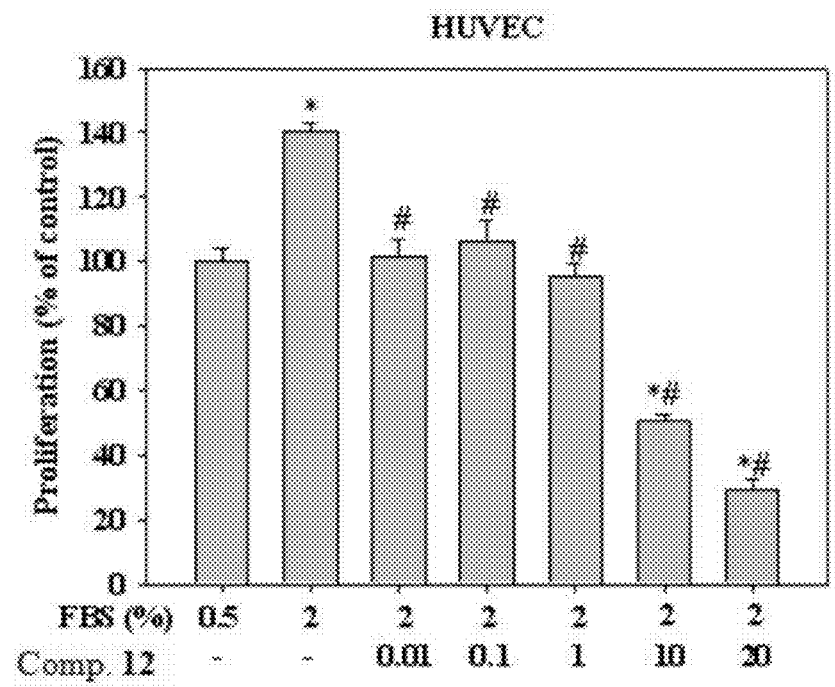
FIG. 3 illustrates a measurement result of a VEGF-induced growth inhibitory effect of the compound 12 on HUVEC cells.

HUVEC cells were cultured in a flask coated with 0.2% gelatin. Then, the HUVEC cells were cultured in an endothelial cell basal medium-2 (EBM-2, Clonetics, San Diego, Calif.). This EBM-2 contained fetal bovine serum (FBS), hydrocortisone, a human basic fibroblast growth factor (hFGF-B), a vascular endothelial growth factor (VEGF), a human recombinant insulin-like growth factor (R3-IGF-1), ascorbic acid, a human epidermal growth factor (hEGF), GA-1000, and heparin. The HUVEC cells were cultured for 4 to 5 days and injected into a 24-well plate in a density of 5×10$^4$ cells/well, and the media of the respective wells were set at 1 ml. In order to test the effect of the compound 12 in endothelial cells induced by the VEGF, the HUVEC cells were treated with a mixture of the VEGF and the compound 12 and cultured for 24 hours, and, then, 100 μl of MTT 3-(4,5-dimethylthiazol-2-yl)-2,5-diphenyl tetrazolium bromide; 5 g MTT/1 in H$_2$O) was added thereto and further cultured for 4 hours. Then, 200 μl of dimethylsulfoxide (DMSO) was added to the respective wells containing the corresponding cells and mixed with a pipette to dissolve the reduced MTT crystals. Relative cell survival rates were measured by scanning with a microplate reader (Molecular Devices, Menlo Park, Calif.) having 540 nm filter. As illustrated in FIG. 3, the compound 12 of the present invention reduced VEGF-induced cell growth in a concentration-dependent manner.

Experimental Example 3

Chemostatic Migration Inhibitory Effect in HUVEC Cells

Figure 4:
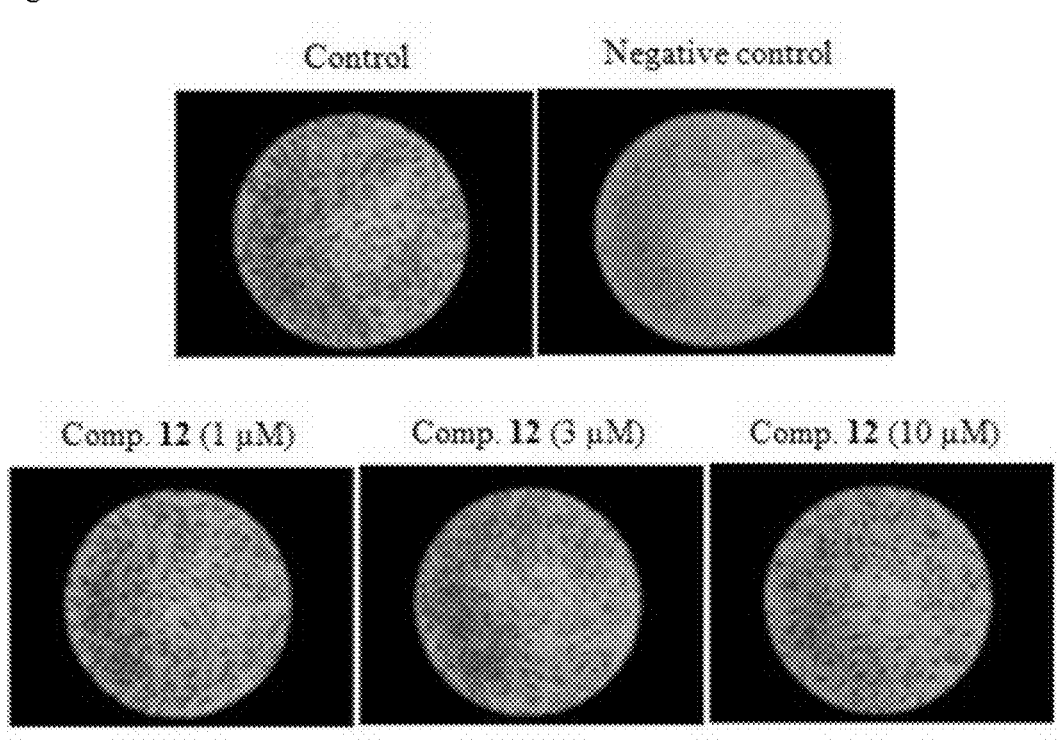
FIG. 4 provides photomicrographs taken at a magnification of 200 times of a bottom side of a polycarbonate filter in order to check an infiltration inhibitory effect of the compound 12 on HUVEC cells.

In order to examine a chemostatic migration inhibitory effect of the compound of the present invention, the following in vitro experiment was carried out using HUVEC cells (Mi-Sung Kim et al., Cancer Research, 63, 5454-5461, 2003; Sang-Oh Yoon et al., The Journal of Biological Chemistry, 276, 20085-20092, 2001; Sonia Zorzet et al., The Journal of Pharmacology and Experimental Therapeutics, 295, 927-933, 2000). A culture plate applied hereto was a 24-well plate (Corning Costar, Cambridge, Mass.) including a polycarbonate filter having a plurality of pores of 8 mm in size. The bottom side of the polycarbonate filter was coated with 20 l of type I collagen in a concentration of 0.5 mg/ml, and the top side thereof was coated with 20 l of matrigel (BD Bioscience, Bedford, Mass.) in a concentration of 1.5 mg/ml. Here, the lower region of the polycarbonate filter was filled with a medium including 2% FBS, and the HUVEC cells were inoculated into the upper region of the polycarbonate filter. In this case, the compound 12 was dissolved in dimethyl sulfoxide (DMSO) and diluted with phosphate buffered saline (PBS) by concentrations (1, 3, 10 μM). The HUVEC cells inoculated as such were cultured at 37° C. for 24 hours. Subsequently, the cells infiltrating the bottom side of the polycarbonate filter were fixed with methanol and stained with hematoxylin and eosin. FIG. 4 provides photomicrographs taken at a magnification of 200 times of the bottom side of the polycarbonate filter in order to check an infiltration inhibitory effect of the compound 12 on HUVEC cells. Herein, in the case of a treatment with the compound 12 of the present invention, it could be seen that cancer cells infiltrating the bottom side of the polycarbonate filter was remarkably decreased as compared with the control group, and, thus, it could be seen that the compound 12 of the present invention reduced infiltration of the HUVEC cells in a concentration-dependent manner.

Experimental Example 4

Measurement of Reactive Oxygen Species (ROS) Scavenging Effect in HUVEC Cells

Figure 5:
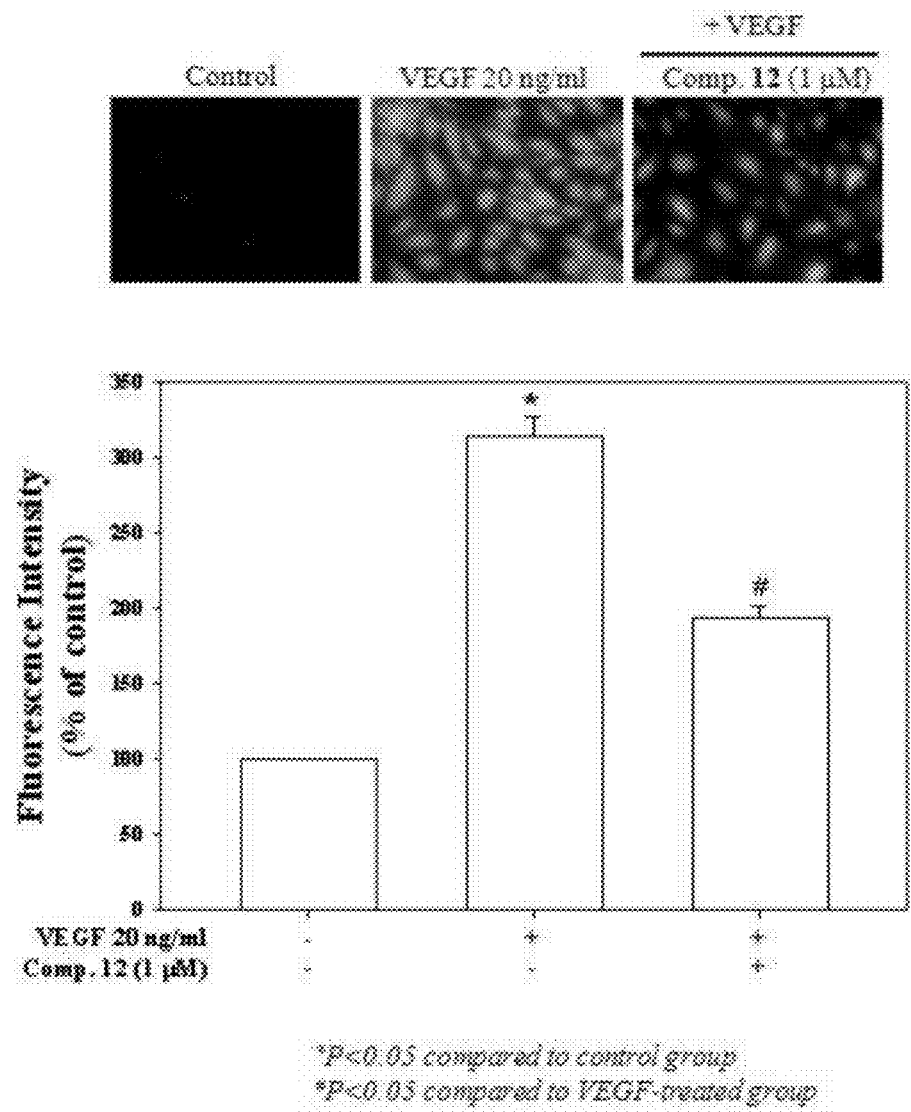
FIG. 5 provides photomicrographs taken at a magnification of 400 times of cells in order to check an ROS scavenging effect of the compound 12.
Figure 6:
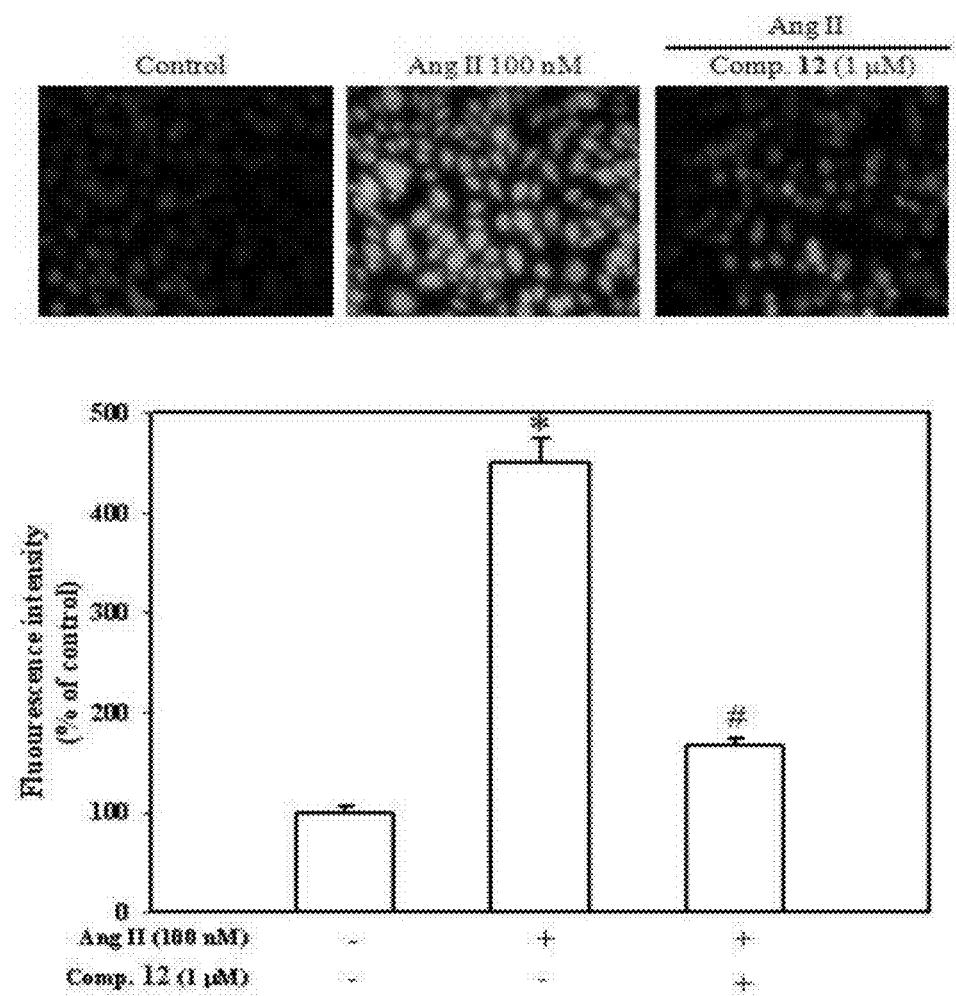
FIG. 6 illustrates an observation result of the ROS scavenging effect of the compound 12 by treating the adult retinal pigment epithelium (ARPE)-19 cell line with angiotensin II, which is a risk factor of macular degeneration.
Figure 7:
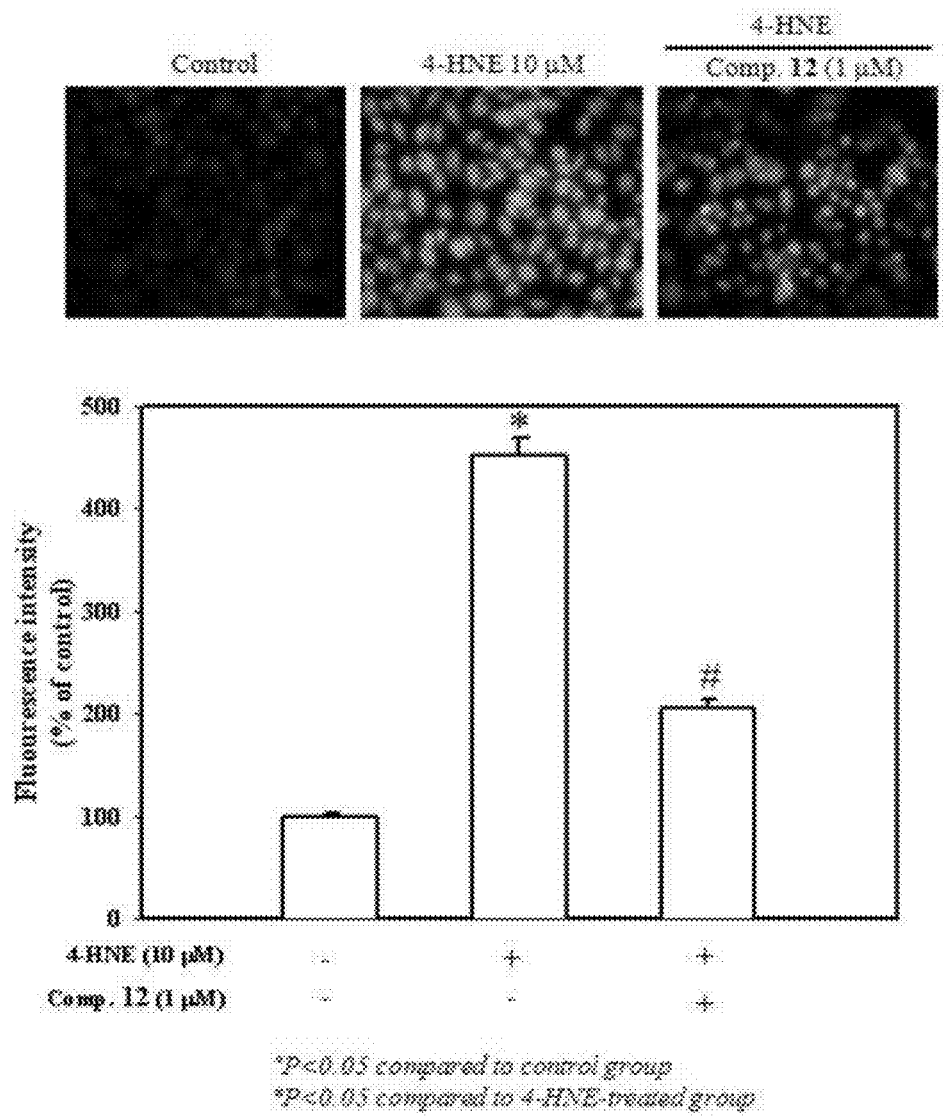
FIG. 7 illustrates an observation result of the ROS scavenging effect of the compound 12 by treating the adult retinal pigment epithelium (ARPE)-19 cell line with 4-hydroxynonenal (4-HNE), which is a risk factor of macular degeneration.

In order to measure an ROS scavenging effect in HUVEC cells induced by a VEGF, 2',7'-dichlorofluorescein diacetate (DCF-DA) was used. When the ROS was present in cells, the DCF-DA was oxidized to fluorescent DCF exhibiting green fluorescence. The HUVEC cells were injected into 8-well plates coated with 0.2% gelatin in a density of $1\times10^5$ cells/well and then cultured for 24 hours. A pre-treatment was carried out to the compound 12 for 3 hours and induced by the VEGF for 15 minutes and washed with PBS (pH 7.4) three times. Then, 10 μM DCF-DA was put into an EBM-2 and used to treat in darkroom for 30 minutes, and then washed again with the PBS three times. A fluorescence degree of the cells was measured using a fluorescence microscope. FIG. 5 provides photomicrographs taken at a magnification of 400 times of cells in order to check an ROS scavenging effect of the compound 12 of the present invention. Herein, in the case of a treatment with the compound 12 of the present invention, it could be seen that a fluorescence degree of the cells was remarkably decreased as compared with the VEGF. FIG. 6 and FIG. 7 illustrate an observation result of the ROS scavenging effect of the compound 12 by treating the adult retinal pigment epithelium (ARPE)-19 cell line with 4-hydroxynonenal (4-HNE) or angiotensin II, which is a risk factor of macular degeneration. Likewise, it could be seen that a fluorescence degree of the cells was remarkably decreased as compared with the control group. The 4-hydroxynonenal (4-HNE) or angiotensin II, which is a risk factor of macular degeneration caused cell damage by generation of ROS in ARPE cell and caused damage of a Bruch's membrane and angiogenesis, resulting in macular degeneration and loss of eyesight. Based on the above experimental result, the compound 12 strongly inhibits generation of ROS of 4-hydroxynonenal (4-HNE) or angiotensin II and thus can be expected to be effective in treating macular degeneration.

Experimental Example 5

Angiogenesis Caused by Tumorigenesis and Tumor Growth Inhibitory Effect

FIG. 8 illustrates an observation result of angiogenesis caused by tumorigenesis by inoculating A549 lung cancer cells to a CAM and a tumor growth inhibitory effect. Fertilized chicken eggs were cultured, and on the ninth day, a window was made in the same manner, and instead of a disc, cancer cells were mixed with matrigel at a ratio of 1:1 and treated with the compound 12 and inoculated in a density of $1.5\times10^6$ cells/CAM. After 5 days from the inoculation, a CAM portion, in which tumor was formed, was separated and washed with PBS to take images using a stereomicroscope (Stemi SV6 stereomicroscope, Carl Zeiss, Germany) and Image-Pro Plus software (Media Cybernetics; Silver Spring, Md., USA). Then, the number of branches was counted and the result data were analyzed. As a result thereof, the compound 12 of the present invention inhibited angiogenesis caused by tumorigenesis and also inhibited tumor growth in a significantly low concentration as compared with α-tocopherol as the control group.

Experimental Example 6

Toxicity Experiment

The compound 12 was suspended in a 0.5% methyl cellulose solution and orally administered to male Balb/c mice with a single dose of 0.5 g/kg, 1 g/kg, and 2 g/kg. Then, the survival rate and weights of the mice were checked for 7 days.

After the administration, whether the animal was dead or not, clinical symptoms, changes in weight were observed, and a hematological test and a blood chemical test were carried out. Further, the mice were autopsied, and then, whether or not abdominal and chest organs are abnormal was observed with the naked eye.

As a result thereof, any especially remarkable clinical symptoms were not observed from the animals, and no animal was dead. No change in toxicity was observed from the weight change, the hematological test, the blood chemical test, and the postmortem report.

According to the above result, the compounds of the present invention with a dose of up to 2 g/kg did not exhibit a change in toxicity in the mice, and, thus, they were determined as safe substances having a median lethal dose ($LD_{50}$) of more than 2 g/kg for oral administration.

Hereinafter, the formulation examples of the composition containing the compound 12 according to the present invention will be explained, however, which should not be limited thereto. Rather, these examples are provided no more than to explain the present invention in more detail.

Formulation Example 1

Preparation of Powders 20 mg of the compound 12, 100 mg of lactose, and 10 mg of talc were mixed with one another and packed in an airtight bag, thus preparing a powder.

Formulation Example 2

Preparation of Tablets 20 mg of the compound 12, 100 mg of corn starch, 100 mg of lactose, and 2 mg of magnesium stearate were mixed with one another and tableted according to a conventional method of preparing tablets, thus preparing a tablet.

Formulation Example 3

Preparation of Capsules 10 mg of the compound 12, 100 mg of corn starch, 100 mg of lactose, and 2 mg of magnesium stearate were mixed with one another and packed in a gelatin capsule according to a conventional method of preparing capsules, thus preparing a capsule.

Formulation Example 4

Preparation of Injections 10 mg of the compound 12, sterile distilled water for injection in a proper amount, and a pH regulator in a proper amount were mixed with one another, and then, an injection was prepared to 2 ml of an ampoule containing the above ingredients according to a conventional method of preparing injections.

Formulation Example 5

Preparation of Ointments 10 mg of the compound 12, 250 mg of PEG-4000, 650 mg of PEG-400, 10 mg of white vaseline, 1.44 mg of Methyl para-oxybenzoate, 0.18 mg of Propyl para-oxybenzoate and a balance of distilled water were mixed with one another, and then, an ointment was prepared according to a conventional method of preparing ointments.

Specific parts of the present invention have been described in detail, and, thus, it is obvious to those skilled in the art that such detailed descriptions are provided as preferable aspects but do not limit the scope of the present invention. Therefore, the scope of the present invention should be considered in light of the appended claims and equivalent arrangements.

The invention claimed is:

1. A method of inhibiting angiogenesis which supports growth and metastasis of a lung cancer, comprising:
administering to a subject a pharmaceutical composition comprising a therapeutically effective amount of bicyclic pyridinol derivative expressed by the following Chemical Formula:

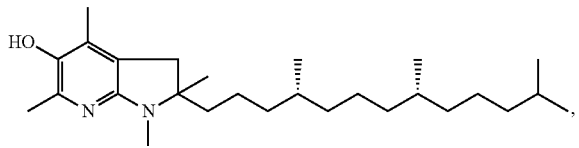

wherein the angiogenesis supporting the growth and metastasis of the lung cancer is inhibited in the subject.
2. The method of claim 1, wherein,
the pharmaceutical composition inhibits a tumor growth, which is supported by the angiogenesis.

* * * * *